Figure 1:
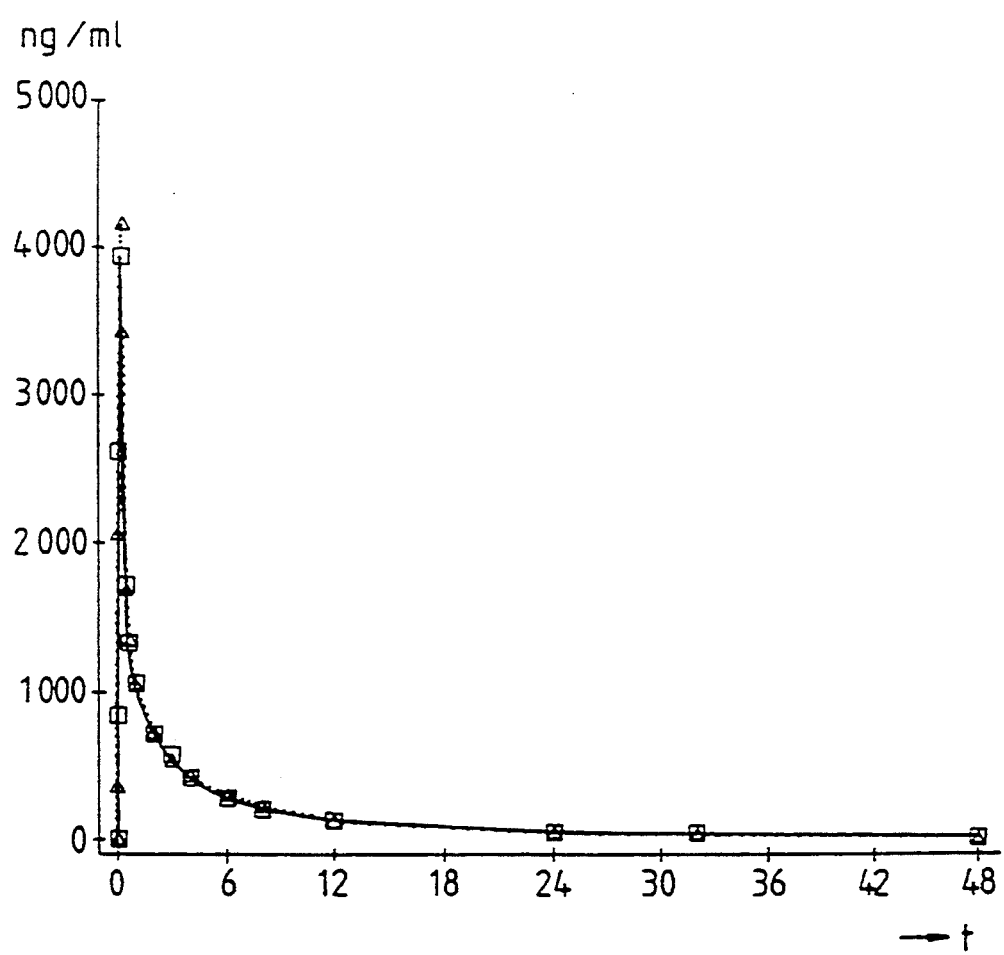

United States Patent [19]

List et al.

[11] Patent Number: 5,389,382

[45] Date of Patent: Feb. 14, 1995

[54] HYDROSOLS OF PHARMACOLOGICALLY ACTIVE AGENTS AND THEIR PHARMACEUTICAL COMPOSITIONS COMPRISING THEM

[75] Inventors: Martin List; Heinz Sucker, both of Basel, Switzerland

[73] Assignee: Sandoz Ltd., Basel, Switzerland

[21] Appl. No.: 642,106

[22] Filed: Jan. 16, 1991

Related U.S. Application Data

[63] Continuation of Ser. No. 436,147, Nov. 13, 1989, abandoned, which is a continuation of Ser. No. 134,337, Dec. 17, 1987, abandoned.

[30] Foreign Application Priority Data

Dec. 19, 1986 [DE] Germany ............... 3643392

[51] Int. Cl.$^6$ .................. A61K 9/14; A61K 9/16; A61K 9/50; A61K 37/02
[52] U.S. Cl. .................. 424/499; 424/423; 424/489; 514/11; 514/937
[58] Field of Search ............ 424/422, 423, 484, 489, 424/499; 514/11, 937

[56] References Cited

U.S. PATENT DOCUMENTS 4,117,118 9/1978 Härri et al. .
4,540,602 10/1985 Motoyama et al. .

FOREIGN PATENT DOCUMENTS 0169618 1/1985 European Pat. Off. .
1516348 7/1978 United Kingdom .

OTHER PUBLICATIONS

List et al., "Pharmaceutical Injectable Hydrosols containing Water-insoluble active agents", 63-6, Pharmaceuticals, 1988.

Primary Examiner—Thurman K. Page
Assistant Examiner—Carlos Azpuru
Attorney, Agent, or Firm—Robert S. Honor; Melvyn M. Kassenoff; Carl W. Battle

[57] ABSTRACT

The invention provides a hydrosol of a pharmacological active agent in an intravenous applicable, stabilised, pharmaceutically acceptable form, which form is suspended or is dry and re-suspendable in an aqueous medium.

The hydrosol contains solid active agent particles, e.g. of dihydropyridines or cyclosporines.

15 Claims, 1 Drawing Sheet

HYDROSOLS OF PHARMACOLOGICALLY ACTIVE AGENTS AND THEIR PHARMACEUTICAL COMPOSITIONS COMPRISING THEM

This is a continuation of application Ser. No. 07/436,147, filed Nov. 13, 1989, now abandoned, which in turn is a continuation of application Ser. No. 07/134,337, filed Dec. 17, 1987, now abandoned.

This invention relates to hydrosols of pharmacologically active agents, suspended or re-suspendable in an aqueous medium.

Hydrosols have been generally known for a long time. Their solid particles have diameters in the nanometer range, varying from about 1 nanometer ($=10^{-9}$ meter) to about 10,000 nanometer ($=10^{-4}$ micrometer), preferably to 1 micrometer.

They can be made visible using the Tyndall effect.

The invention relates especially to a hydrosol of a pharmacologically, active agent in an intravenously applicable, stabilized pharmaceutically acceptable form, which form is suspended or is re-suspendable in an aqueous medium and is characterised in that the hydrosol comprises solid particles of the active substance.

Hydrosols in an intravenously applicable pharmaceutical composition form have been proposed in the UK Patent Specification No. 1,516,348. Their particles are suitably modified and have an appropriate diameter in the nanometer range and aqueous suspensions thereof can be injected through a needle and on administration are taken up in the blood circulation. The suspended particles are sufficiently small to flow through blood vessels. They are also stabilized to avoid aggregation.

The particles described in the above-mentioned UK Patent Specification are colloid nanoparticles. Their colloid material is cross-linked, e.g. cross-linked gelatine or a cross-linked cellulose derivative. The colloid particles clearly contain a water soluble or water-insoluble pharmacologically active agent in molecular distribution since during their preparation, the dissolved active agent is not allowed to precipitate (p.5, l.121–p.6 l.10).

After administration as a suspension the pharmacologically active agent is released from the nanoparticles at a slow rate.

The invention provides in particular a hydrosol of solid active agent particles in such a form which, when in water suspended and administered, behaves, regarding pharmacological activity, as an injectable solution, If pharmacologically analysed in the blood plasma, the pharmacological compound is detectable from a hydrosol of the present invention as soon as from an administered conventional injectable solution.

Hitherto it was never proposed to use pharmacologically active agent particles in an aqueous hydrosol form for intravenous injection purposes.

The active agent hydrosol particles of the invention preferably have an average statistical diameter of between 1 micrometer and 1 nanometer, especially between 0.5 micrometer and 1 nanometer.

Active agents for the hydrosols of the invention have preferably a water solubility of below 0.5 g/100 ml, especially below 0.1 g/100 ml at room temperature.

Active agents in this solubility range are e.g. dihydropyridines, especially those having the structure of a 4-aryl-1,4-dihydro-2,6-dialkyl-3,5-pyridine dicarboxyl ester, e.g. Isradipine=isopropyl methyl-4-(2,1,3-benzoxadiazol-4-yl)-1,4-dihydro-2,6-dimethyl-3,5-pyridine carboxylate or Darodipine=diethyl-4-(2,1,3-benzoxadiazol-4-yl) -1,4-dihydro-2,6-dimethyl-3,5-pyridine dicarboxylate.

Darodipine and Isradipine are e.g. known from the european patent specification No. 150 and the UK patent specification No. 2,037,766 respectively.

The dihydropyridines are calcium antagonists and are particularly used as anti-hypertensives and for the treatment of Angina pectoris.

For their use as anti-hypertensives e.g. up to 250 mg preferably up to 200 mg, especially up to about 50 to 100 mg Darodipine and up to 50 mg, preferably up to 25 mg e.g. 5 to 20 mg Isradipine are administered orally a day, e.g. 2.5 mg Isradipine twice a day. They can also be administered intravenously, e.g. from 0.5 to 2 mg over 30 minutes, e.g. in the case of Isradipine.

Other active substances in the mentioned solubility range include cyclosporins, especially Cyclosporin A, having a water solubility of below 0.004 g/100 ml or Proquazone=1-isopropyl-7-methyl-4-phenyl-2(1H)-quinazolone, having a water solubility of below 0.1 g/100 ml.

Further examples of compounds in the low water solubility range are steroids.

The cyclosporins comprise a class of structurally distinct, cyclic, poly-N-methylated undecapeptides having valuable pharmacological, in particular immunosuppressive, anti-inflammatory and anti-parasitic, in particular anti-protozoal activity. The first of the cyclosporins to be isolated and the "parent" compound of the class, is the naturally occurring fungal metabolite cyclosporin, also known as cyclosporin A, the production and properties of which are described e.g. in U.S. Pat. No. 4,117,118.

Since the original discovery of Cyclosporin a wide variety of naturally occurring cyclosporins have been isolated and identified and many further non-natural cyclosporins have been prepared by synthetic or semi-synthetic means or by the application of modified culture techniques. The class comprised by the cyclosporins is thus now substantial and includes, for example, the naturally occurring cyclosporins (Thr$^2$)-, (Val$^2$)- and (Nva$^2$)- Cyclosporin (also known as cyclosporins C, D and G respectively), as well as various semi-synthetic derivatives thereof, such as their dihydro derivatives (e.g. as disclosed in U.S. Pat. Nos. 4,108,985; 4,210,581 and 4,220,641) including e.g. (Dihydro-MeBmt$^1$)-(Val$^2$)-Cyclosporin (also known as dihydrocyclosporin D) and other natural and artificial cyclosporins such as those disclosed in European Patent Publication NO. 0,058,134 B1, for example [(D)-Ser$^8$]-Cyclosporin; UK Patent Application No. 2,115,936 A, for example [O-Acetyl-(D)-Ser$^8$]-Cyclosporin; and European Patent Application No. 86810112.2, for example [Val]$^2$-[(D)Methylthio-Ser]$^3$- and [Dihydro-MeBmt]$^1$-[Val]$^2$-[(D)-Methylthio-Sar]$^3$-Cyclosporin.

[In accordance with now conventional nomenclature for the cyclosporins, these are defined herein by reference to the structure of Cyclosporin (i.e. cyclosporin A). This is done by first indicating those residues in the molecule which differ from those present in Cyclosporin and then applying the term "Cyclosporin" to characterise the remaining residues which are identical to those present in Cyclosporin. Cyclosporin has the formula I

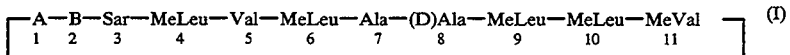

wherein A represents the [N-methyl-(4R)-4-but-2E-en-1-yl-4-methyl-(L)threonyl] residue of formula II

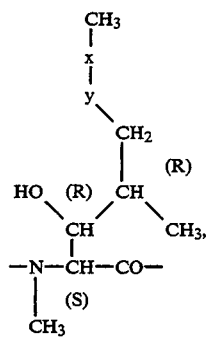

which residue is abbreviated as —MeBmt— and in which —x—y— is —CH=CH—(trans), B is the alpha-aminobutyric acid residue, abbreviated as —alphaAbu—. Accordingly (Thr$^2$)-Cyclosporine (Cyclosporin C) is the compound of formula I, wherein A has the meaning given above and B is —Thr—, and (Dihydro-MeBmt$^1$)-(Val$^2$)-Cyclosporin (Dihydrocyclosporin D) is the compound of formula I, wherein A represents the -dihydro-MeBmt-residue of formula II above in which x—y— is —CH$_2$—CH$_2$—, and B is Val-].

As the "parent" compound of the class, Cyclosporin has so far received the most attention. The primary area of clinical investigation for Cyclosporin has been as an immunosuppressive agent, in particular in relation to its application to recipients of organ transplants, e.g. heart, lung, combined heart-lung, liver, kidney, pancreatic, bone-marrow, skin and corneal transplants and, in particular, allogenic organ transplants. In this field Cyclosporin has achieved a remarkable success and reputation and is now commercially available and widely employed in clinic.

At the same time, applicability of Cyclosporin to various autoimmune diseases and to inflammatory conditions, in particular inflammatory conditions with an aetiology including an autoimmune component such as arthritis (for example rheumatoid arthritis, arthritis chronica progrediente and arthritis deformans) and rheumatic diseases, has been intensive and reports and results in vitro, in animal models and in clinical trials are wide-spread in the literature. Specific autoimmune diseases for which Cyclosporin therapy has been proposed or applied include, autoimmune hematological disorders (including, e.g. hemolytic anaemia, aplastic anaemia, pure red cell anaemia and idiopathic thrombocytopaenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease) endocrine opthalmopathy, Graves disease, sarcoidosis, multiple sclerosis, primary billiary cirrhosis, primary juvenile diabetes (diabetes mellitus type I), uveitis (anterior and posterior), interstitial lung fibrosis, psoriatic arthritis and glomerulonephritis (with and without nephrotic syndrome, e.g. including idiopathic nephrotic syndrome or minimal change nephropathy).

A further area of investigation has been potential applicability as an anti-parasitic, in particular anti-protozoal agent, with possible uses suggested including treatment of malaria, coccidiomycosis and schistosomiasis.

Other cyclosporins exhibit the same overall pharmacological utility as Cyclosporin and various proposals for application, in particular in one or other of the above identified indications, are prevelant in the literature, e.g. when cyclosporin is not well tolerated, e.g. because of hepatoxicity or nephrotoxicity in certain patients.

Cyclosporin is especially useful in the field of transplant surgery and of autoimmune diseases where it is administered orally in amounts of about 50 to about 900 mg, preferably in divided amounts, 2 to 4 times a day, of dosage units of 12 to 450 mg. It can also be administered intravenously e.g. from 225 to 375 mg per day, using a 1:20 to 1:100 aqueous dilution of a concentration in ampoules which contain 1 or 5 ml of a solution which contains 50 mg Cyclosporin/m.

The invention also provides a hydrosol comprising solid particles of a cyclosporin or of a dihydropyridine in a stabilized, pharmaceutically acceptable form, which form is suspended or is dry and re-suspendable in an aqueous medium.

In order to inhibit an increase in the size of the particles of active agent in water, e.g. to prevent an increase in the size of the larger particles at the expense of the smaller particles, a stabilizer is preferably added, which maintains the size distribution of the active hydrosol particles in the dispersion constant. The stabilizer can be a second particulate phase.

In the case of e.g. dihydropyridines, like Darodipine, Isradipine, or of Proquazone, ethyl cellulose is preferably selected as the stabilizer, although this compound also can be substituted partially by gelatin, which is another, better pharmaceutically acceptable, stabiliser type: Of ethyl cellulose preferably a low viscosity variante is chosen, e.g. of 22 cps or e.g. 7 cps (centipoise).

In the case of cyclosporins, e.g. Cyclosporin A, a gelatin is preferably selected, especially a modified gelatin, e.g. the plasma expander Gelafundin$^R$, or a gelatin of a highly purified collagen hydrolysate which is soluble in cold water.

In general the weight ratio of active agent to stabiliser is conveniently from about 1:1 to 1:50 and the weight ratio of active agent to water is conveniently from about 1:300 to 1:1500.

For Darodipine or Isradipine the weight ratio of active agent:ethyl cellulose is preferably from 1:1 to 1:4, especially 1:2.5; in the case of Proquazone it is preferably from 1:3 to 1:5, especially 1:4.

For Darodipine, Isradipine or Proquazone the weight ratio of active substance:water is preferably from 1:400 to 1:600, and is in particular 1:500.

For cyclosporins, like Cyclosporin A the weight ratio of active agent:gelatin is preferably from 1:5 to 1:30 and particularly from 1:10 to 1:30 and especially 1:20 for Cyclosporin A.

Additionally, to the stabiliser, an acid is also preferably added as a peptisator, e.g. succinic acid or citric acid.

In the case of citric acid, the weight ratio of active substance:citric acid is preferably from 1:8 to 1:12, and is especially 1:10.

Also for cyclosporins, like Cyclosporin A the weight ratio of active agent:water is preferably from 1:800 to 1:1200, such as 1:1000. However, a dry hydrosol, e.g. in the form of a lyophilisate may also be used, especially of cyclosporins, like Cyclosporin A.

When preparing a dry hydrosol, e.g. in the form of a lyophilisate, a carrier is preferably added, e.g. dextrane, saccharose, glycine, acetose, polyvinylpyrrolidone or particularly a polyol, especially mannitol. Convenient weight ratios of the active agent to the carrier may be from about 1:20 to about 1:100. In the case of mannitol, the weight ratio of active substance:mannitol is preferably from 1:40 to 1:60, especially 1:50.

When drying, e.g. on lyophilisation, the liquid hydrosol, the carrier forms a network structure, which keeps the hydrosol particles separate and prevents their agglomeration.

The invention also provides a process for the production of a hydrosol of a pharmacologically active agent in an intravenously applicable, stabilised, pharmaceutically acceptable form, which form is suspended or is dry and resuspendable in an aqueous medium.

Such a process is known from the above mentioned UK patent specification No. 1,516,348. The cross-linked active agent containing nanoparticles, described in the citation, are prepared by dissolving the carrier for the nanoparticles, like gelatine or serum albumin, as a colloidal solution in water and submitting the carrier to a so-called desolvation process to form the nanoparticles. The desolvation can be effected by the addition of salts, e.g. Na$_2$SO$_4$, and/or by an alcohol, so that the resultant colloid particles have nanoparticle dimensions. Preferably their size is regulated by the addition of an alcohol.

Up till this stage the active agent may be added to the colloid system: as an aqueous solution, if it is water soluble or as an organic solution, if it is difficultly soluble in water. Preferably the active agent is dissolved then in an alcohol, which is used for regulating the desolvation stage of the colloid.

It is believed that in the prior art process the colloid nanoparticles formed from the carrier bind the molecules of active agent by cohaesion. No solid active agent particles are formed.

The thus formed suspension is not suitable as an injectable solution because it contains a alcohol and/or salt in an unacceptable concentration which must be washed out. The washing would, however, convert the resultant colloid particles into a colloid solution again because the colloid nanoparticles would destabilise. Such destabilisation may be avoided by cross-linking the carrier of the colloid nanoparticles, e.g. with an aldehyde, thereby fixing their size and giving stability.

After cross-linking and washing the system is ready for use and, in lyophilisated, re-suspendable state, storable.

According to the present invention active agent hydrosol particles may be prepared, which from a pharmacokinetic and a pharmacodynamic viewpoint, are as fast acting and behave like an injection solution.

The hydrosol particles according to the invention are prepared by a process different from the prior art process.

The present invention provides a process, characterised in that a solution in an organic solvent miscible with water of an active agent difficultly soluble in water is mixed with a comparatively large amount of water under conditions such that a colloid, insoluble in water, is present in the organic solvent and/or a water soluble colloid is present in the water thereby stabilizing the hydrosol of active agent to be formed, and a hydrosol of solid active substance particles is formed, which, if desired, is dried to a form, which is re-suspendable in water.

One difference from the prior art process is that the hydrosol particles are active agent particles and not cross-linked gelatine or albumine particles. Also the hydrosol particles are bound—when a water soluble colloid stabilizer is used—to exchangeable colloid molecules or—when a water insoluble colloid stabilizer is used—to solid—but non cross-linked—colloid particles.

Other differences are, that the desolvation process used in the prior art, the removal of salts and the chemical cross-linking are superfluous.

The novel hydrosol forms may particularly be prepared as follows: a solution of the active agent in a solvent which is miscible with water, e.g. in alcohol, e.g. ethanol or isopropanol, or in acetone, is mixed with a comparatively large amount of water, under such conditions that a hydrosol is produced.

Mixing preferably is effected rapidly to promote formation of the particles at the same time and in a narrow size distribution. A narrow size distribution is desirable to inhibit a re-distribution of the particles taking place in the suspension with the larger particles growing at the expense of smaller ones (=Ostwald ripening) with the result that the hydrosol would become more and more unstable. Rapid mixing also produces large numbers of colloidal particles.

Permanent fixing of the particle size however is possible if the influence of the organic solvent in which the active agent was dissolved is minimalised and for that reason the solvent is preferably removed.

Removal may take place by evaporation, e.g. in a rotary evaporator. The hydrosol suspension, when practically free from organic solvent, may be used for intravenous injection.

However, evaporation can also be continued so that the water of the hydrosol is also evaporated. Preferably this is effected by lyophilisation, so as to facilitate redispersibility.

Upon complete evaporation of the water, a dry lyophilisate may be formed, especially with Cyclosporin A, gelatin, mannitol and acid additive. Such a lyophilisate is especially suitable for maintaining the stability of the hydrosol over a longer period.

The lyophilisate is a starting material for the preparation of pharmaceutical compositions of different types and may e.g. be redispersed with distilled water, leading to a suspension of hydrosol particles having the same size distribution as of the original hydrosol. In suspension form it may be intravenously administrable. The dose of active agent is in general of the same order as used for the same active agent in conventional i.v. solutions.

The invention thus also provides the use of the hydrosol for the preparation of a pharmaceutical composition containing the hydrosol as an active agent, as well as the pharmaceutical compositions containing such hydrosols.

The invention also provides the corresponding pharmaceutical compositions, for use in the treatment of diseases, e.g. of hypertension or Angina pectoris, if they contain the dihydropyridine hydrosols as active agents or for use as an immunosuppressivum or in the treatment of autoimmune diseases, inflammation conditions or diseases with an autoimmune component or of parasitic infections, using the pharmaceutical composition, if they contain the cyclosporin hydrosols as active agents.

The invention also provide the method of treatment using the corresponding pharmaceutical compositions.

The following examples illustrate the invention.

EXAMPLE 1

1 g of ethyl cellulose N7 (Dow Chemical) and 0.4 g of darodipine are dissolved in 40 ml of 94% ethanol.

This solution is rapidly poured into 200 ml of distilled water of 20° C. whilst stirring vigorously.

Ethanol is evaporated off over 5 mins. under reduced pressure at 50° C. in a rotary evaporator.

Any coarse particles which are precipitated are separated by filtration (paper filter with a pore size of 5 micrometers, Schleicher & Schüll).

The average diameter of the particles is 0.116 micrometers. The polydispersity factor is 28%. The measurements were made on a Malvern Submicron Particle Analyser Type 4600 SM.

EXAMPLE 2

0.2 g of Cyclosporin A are dissolved in 8 ml 94% ethanol. The solution is filtered through a 0.2 micrometer membrane, and is injected through an injection needle into a vigorously stirred solution of a temperature of 20° C. and consisting of 10.0 g of mannitol, 4.0 g of gelatin (Stoess) of a quality which is soluble in cold water, and 2.0 g of citric acid in distilled water.

Appropriate quantities are then filled into suitable containers and lyophilised.

EXAMPLE 3

0.8 g of ethyl cellullose (N22 Hercules) are dissolved in 29 ml of 94% ethanol, which contains 0.2 g of proquazone, and then poured whilst stirring into 100 ml of distilled water of 70° C. The ethanol is subsequently evaporated off for 5 mins. at 50° C., under reduced pressure, in a rotary evaporator.

The average diameter of the particles is 0.152 micrometers and the polydispersity factor is 2.

The measurement was carried out using the "Nanosizer" from the company Coulter, which has the same measuring principle as the above-mentioned measuring device.

In this device, the polydispersity factor is a dimensionless unit of measurement for the extent of particle size distribution, whereby 0 is mono-disperse and 9 is very large variation in particle size.

EXAMPLE 4

1 g of ethyl cellulose N7 (Dow Chemical) and 0.4 g of progesterone are dissolved in 40 ml of 94% ethanol.

The solution is rapidly poured into a vigorously stirred solution, consisting of 4.0 g of gelatin of a quality which is soluble in water, in 200 ml of distilled water.

The mixture is treated further as described in Example 1. The average diameter of the particles is 0.245 micrometer, measured as described in Example 3.

EXAMPLES 5–8

Example 1 is repeated with the difference, that 0.4 g of darodipine is substituted by:

0.4 g of progesterone or
0.4 g of dexamethasone acetate or
0.4 g of beclomethasone dipropionate or
0.4 g of fluocinolon acetonide The average diameters of the prepared particles are:
0.140 micrometers
0.140 "
0.145 "
0.140 "
respectively.

The polydispersity factor is 3 for all particles.

EXAMPLE 9

1 g of ethyl cellulose and 0.4 g beclomethasone dipropionate are dissolved in 20 ml of 94% ethanol.

The solution is rapidly poured into a vigorously stirred solution, consisting of 0.2 g of a collagen hydrolysate of a quality which is soluble in cold water, in 100 ml of water.

The mixture is treated further as described in Example 1. The average particle diameter is 0.12 g mikrometer measured as described in Example 3.

EXAMPLE 10

1 g of ethyl cellulose N7 (Dow Chemical) and 0.4 g of isradipine are dissolved in 40 ml of 94% ethanol.

The solution is rapidly poured into a vigorously stirred solution, consisting of 10.0 g of mannitol and 2.0 g of citric acid in 200 ml of a plasma expander on gelatin basis.

The mixture is treated further as described in Example 1. The average particle diameter is 0.320 micrometers measured as described in Example 3.

Subsequently appropriate amounts of liquid are filled into suitable containers and lyophilised.

For usage, the lyophilisates are re-dispersed with distilled water.

EXAMPLE 11

In tests using 5 anaesthetised rabbits, the hydrosol of 2 mg of darodipine in 1 ml of liquid as prepared according to example 1 was compared with a solution of 2 mg of darodipine in a mixture of 2 ml of ethanol and 2 ml of polyethylene glycol 400.

Both samples were diluted with an isotonic glucose solution to a concentration of 100 micrograms per ml.

The animals were given the samples in a quantity of 100 micrograms of active substance per kg body weight, injected over 10 minutes.

In the tests, no significant systemic haemodynamic side-effects of the suspension on the average blood pressure, pulse, blood pressure in the heart ventricle, heart contraction pressure, heart output volume and total peripheral blood circulation were detected, if compared with the true solution.

EXAMPLE 12

Infusions of 20 ml of a re-suspended lyophilisate, prepared according to Example 2 and containing 20.4 mg of Cyclosporin A, and of 20 ml of a solution containing 30 mg Cyclosporin A and polyoxyethylated castor oil and alcohol as solubilisers were administered to four Beagle-dogs in cross-over trial design.

After both infusions the plasma concentrations of cyclosporin A were recorded over 48 hours.

For a true comparison the measured plasma values of the 20.4 mg Cyclosporin infusion were calculated corresponding to a 30 mg infusion and shown in the graph of the accompanying FIG. 1, in which the plasma concentrations are expressed in ng/ml and the time in hours and in which □ is the plasma concentration of the cyclosporin hydrosol Δ is the corresponding concentration of the cyclosporin solution.

No significant differences in the plasma concentrations of both infusion forms were found.

The mean values of each plasma concentration series fell within the standard deviation ranges of the other series.

We claim:

1. A hydrosol which comprises solid particles of a cyclosporin and a stabilizer which maintains the size distribution of said particles, wherein said cyclosporin has a water solubility below 0.5 grams per 100 milliliters, and said particles have a weight ratio of cyclosporin to water of about 1:300 to about 1:1500 and a weight ratio of cyclosporin to said stabilizer of about 1:1 to about 1:50.

2. The hydrosol according to claim 1, wherein said cyclosporin is Cyclosporin A.

3. The hydrosol according to claim 1, wherein the stabiliser is ethyl cellulose.

4. The hydrosol according to claim 1, containing a pharmaceutically acceptable gelatin as the stabiliser.

5. The hydrosol according to claim 1, in the form of a lyophilisate.

6. The hydrosol according to claim 1, containing a carrier wherein the weight ratio of said cyclosporin to said carrier is from about 1:20 to about 1:100.

7. The hydrosol according to claim 1, with an acid additive.

8. The hydrosol of claim 1 wherein said cyclosporin has a water solubility below 0.1 grams per 100 milliliter.

9. The hydrosol of claim 1 wherein said solid particles have an average statistical diameter of between 1 micrometer and 1 nanometer.

10. A dry hydrosol in the form of solid particles comprising a cyclosporin and a stabilizer which maintains the size distribution of said particles, wherein said cyclosporin has a water solubility below 0.5 grams per 100 milliliters of water, and said particles have a weight ratio of cyclosporin to said stabilizer of about 1:1 to about 1:50.

11. The hydrosol of claim 10 wherein said carrier is selected from the group consisting of dextran, saccharose, glycine, acetose, polyvinylpyrrolidone and a polyol.

12. The hydrosol of claim 1 wherein said hydrosol is an aqueous dispersion.

13. A pharmaceutical composition comprising the hydrosol of claim 1 wherein said composition is in an injectable form.

14. The hydrosol of claim 1 wherein said stabilizer is a second particulate phase.

15. A pharmaceutical composition comprising solid particles of a cyclosporin and a stabilizer which maintains the size distribution of said particles, wherein said cyclosporin has a water solubility below 0.5 grams per 100 milliliter, and said particles have a weight ratio of cyclosporin to water of about 1:300 to about 1:1500 and a weight ratio of cyclosporin to said stabilizer of about 1:1 to about 1:50.

* * * * *